(12) United States Patent  
Beasley (10) Patent No.: US 9,517,010 B2
(45) Date of Patent: Dec. 13, 2016

(54) OPHTHALMIC INSTRUMENTS (75) Inventor: Adrian Carl Beasley, Reading (GB)

(73) Assignee: Keelner Limited, Windsor (GB)

( * ) Notice: Subject to any disclaimer, the term of this patent is extended or adjusted under 35 U.S.C. 154(b) by 368 days.

(21) Appl. No.: 13/500,129

(22) PCT Filed: Oct. 1, 2010

(86) PCT No.: PCT/GB2010/051641
§ 371 (c)(1),
(2), (4) Date: Apr. 4, 2012

(87) PCT Pub. No.: WO2011/042723
PCT Pub. Date: Apr. 14, 2011

(65) Prior Publication Data
US 2012/0200690 A1 Aug. 9, 2012

(30) Foreign Application Priority Data
Oct. 5, 2009 (GB) .................................. 0917421.0

(51) Int. Cl.
A61B 3/12 (2006.01)
A61B 3/14 (2006.01)

(52) U.S. Cl.
CPC ............. A61B 3/1208 (2013.01); A61B 3/145 (2013.01)

(58) Field of Classification Search
USPC .......................................................... 348/78
See application file for complete search history.

(56) References Cited

U.S. PATENT DOCUMENTS

| 6,350,031 B1 | 2/2002 | Lashkari et al. |
| 2003/0088169 A1* | 5/2003 | Percival ............... A61B 3/0058 600/399 |
| 2005/0128735 A1 | 6/2005 | Atkins et al. |
| 2006/0017657 A1* | 1/2006 | Yamasaki ......................... 345/8 |
| 2006/0052146 A1* | 3/2006 | Ou ........................ H04M 1/05 455/575.2 |
| 2007/0184422 A1* | 8/2007 | Takahashi ........... G06F 19/3437 434/262 |
| 2007/0248238 A1* | 10/2007 | Abreu .................... G02C 3/003 381/381 |

(Continued)

FOREIGN PATENT DOCUMENTS

| EP | 1938745 A1 | 7/2008 |
| JP | 60-094201 | 6/1985 |

(Continued)

OTHER PUBLICATIONS

English-language abstract of Korean Patent Publication No. KR 20020018320 A, downloaded from http://worldwide.espacenet.com Mar. 22, 2012.

(Continued)

Primary Examiner — Tracy Y Li
(74) Attorney, Agent, or Firm — Dascenzo Intellectual Property Law, P.C.; Ian D. Gates (57) ABSTRACT An ophthalmic instrument for viewing an eye under examination, wherein the instrument includes image capture means (26) for capturing an image of said eye and data processing means (40, 42, 46) for converting said image into a computer readable file, wherein the instrument carries a memory (44, 200), which may be detachable, for storing said file for subsequent transfer to a computer.

20 Claims, 5 Drawing Sheets (56) References Cited

U.S. PATENT DOCUMENTS

| | | | |
|---|---|---|---|
| 2008/0030683 A1 | 2/2008 | Goldfain et al. | |
| 2008/0259274 A1 | 10/2008 | Chinnock | |
| 2009/0153796 A1* | 6/2009 | Rabner | A61B 3/0091 351/201 |
| 2009/0243970 A1* | 10/2009 | Kato et al. | 345/8 |
| 2009/0303435 A1* | 12/2009 | Flitcroft | 351/202 |
| 2010/0328051 A1* | 12/2010 | Hale et al. | 340/407.1 |

FOREIGN PATENT DOCUMENTS

| | | |
|---|---|---|
| JP | S62-500914 | 4/1987 |
| JP | 7-160310 | 6/1995 |
| JP | 11-075142 | 3/1999 |
| JP | 2008-252319 | 10/2008 |
| JP | 2009000363 A | 1/2009 |
| KR | 20020018320 A | 3/2002 |
| WO | WO 00/07496 | 2/2000 |
| WO | WO 00/30528 | 6/2000 |
| WO | WO 03/094706 | 11/2003 |
| WO | WO 2008/040026 | 4/2008 |

OTHER PUBLICATIONS

English-language abstract of Japanese Patent Publication No. JP 2009000363 A, downloaded from http://worldwide.espacenet.com Mar. 22, 2012.
Search Report issued in connection with United Kingdom Patent Application No. GB0917421.0, 2 pages, United Kingdom Intellectual Property Office, Jun. 11, 2010.
International Search Report and Written Opinion, PCT Patent Application No. PCT/GB2010/051641, 12 pages, European Patent Office, Dec. 8, 2010.
English-language abstract of Japanese Utility Model Laying-Open No. 60-094201, Jun. 27, 1985.
English-language abstract of Japanese Patent No. S62-500914, European Patent Office, Apr. 16, 1987.
English-language abstract of Japanese Patent Publication No. 7-160310, Japan Patent Office, Jun. 23, 1995.
English-language abstract of Japanese Patent Publication No. 11-075142, Japan Patent Office, Mar. 16, 1999.
English-language abstract of Japanese Patent Publication No. 2008-252319, Japan Patent Office, Oct. 16, 2008.

* cited by examiner

OPHTHALMIC INSTRUMENTS

FIELD OF THE INVENTION

This invention relates to an ophthalmic instrument and more particularly, but not exclusively, to an indirect ophthalmoscope which can be used to capture images of an eye for use in teaching or for subsequent analysis.

BACKGROUND TO THE INVENTION

Indirect ophthalmoscopy, in particular binocular indirect ophthalmoscopy, is a procedure commonly used to examine the fundus of an eye. The technique involves using a hand-held condensing lens which is placed between the user and the subject. This lens produces an aerial image of the retina that is viewed through the viewing optics of the ophthalmoscope.

Typically, the ophthalmoscope is head mounted and comprises a light source from which a beam is projected towards the eye under examination via the hand-held condensing lens. The viewing optics, which are usually binocular, enable the examiner or user to obtain a view of the image of the fundus of the eye under examination.

Certain ophthalmoscopes, in particular teaching ophthalmoscopes, are provided with video cameras for capturing images of an eye under examination. Those images can be fed to an external computer on which they are recorded for subsequent analysis by a qualified practitioner or by students being taught the technique of indirect ophthalmoscopy. The connection between the computer and the instrument is a cable, such as a USB or firewire cable which can impede the movement of the user. In addition, a cable connection provides a limited bandwidth means of transmitting image data, and the can correspondingly limit the resolution and/or frame rate of the video footage which can be supplied from the instrument to the computer.

SUMMARY OF THE INVENTION

According to the invention there is provided an ophthalmic instrument for viewing an eye under examination, wherein the instrument includes image capture means for capturing an image of said eye and data processing means for converting said image into a computer readable file, wherein the instrument carries a memory for storing said file for subsequent transfer to a computer.

Preferably, the instrument is hand-held or head mounted, in use.

The provision of the memory on the instrument avoids the need for the instrument to communicate with an external computer as the image is being captured. Thus, when in use, the instrument does not have to be connected to the computer via a cable, which may be inconvenient and may even pose a tripping hazard. Nor does the instrument need a radio link, which may be prone to interruption, with the computer.

Preferably, the image capture means comprises a video camera.

In this case, the resolution and frame rate of the captured video footage (i.e. a sequence of captured images) is not limited by the allowable bandwidth of a connection to a computer, since the video data is stored locally, on said memory. For example, USB2 and firewire cable connections provide a data transfer rate of 480M Bits/s which limits the video capture rate to 1.2 MP at 15 frames per second. By contrast, recording onto a locally memory allows a much higher resolution and a higher frame rate dependent only on the choices between the recording hardware.

Conveniently, the memory comprises a portable memory device which is detachable from the instrument and is connectable to a computer to be read thereby.

Thus, once the images and/or footage have been captured by the instrument, they may readily be transferred by removing the device and connecting it to a computer. In addition, the instrument may be used with each of a number of such devices in turn, so that images and/or footage can be transferred from one device which has been removed, whilst fresh images and/or footage are being recorded onto another such device.

Preferably, the detachable memory device is a solid state device, preferably comprising a memory card or USB stick.

Such devices are generally compact, lightweight, robust, cheap, easy to use and are compatible with most computers.

Alternatively, the memory could be built into the instrument, in which case the transferring of the images involves connecting the instrument to a computer which treats the instrument as a mass storage device. Such a connection may be made using a firewire or USB cable, in which case the bandwidth limitations mentioned above will not limit resolution or frame rate of the transferred footage since the transfer can take longer than the duration of the period covered by the footage.

Preferably, the instrument is provided with a display screen (preferably a local display screen) on which the user may view the images being captured by the image capture means.

In addition, the instrument may to advantage also include viewing optics through which the user may view the eye under examination.

Such optics are a feature of conventional instruments, and can provide high resolution images of an eye under examination. Also, for certain types of instrument, such as a binocular indirect ophthalmoscope, the viewing optics provide a stereoscopic view of an eye. In addition, the instrument can still be used with the image capture means and viewing screens switched off, i.e. as a conventional instrument (in which operating mode the power consumption of the instrument is reduced).

Where the viewing optics include an eyepiece, the screen may to advantage be located on the instrument adjacent, for example above, said eyepiece.

Alternatively, the screen may be separate from the body of the instrument and includes means for monitoring and retaining the screen in the vicinity of one of the user's hands.

If the instrument is an indirect ophthalmoscope, the screen can thus be retained in the vicinity of the hand held lens. To that end, the screen may be attached to the lens or provided with a strap or band for attachment of the screen to the user's forearm. Such a band could be similar to the type of band that attaches a personal music player to the arm of somebody who wishes to listen to music while jogging.

The screen is positioned away from the viewer's eye but can still be viewed, through the ophthalmoscope's viewing optics, without the need for any additional accommodation lens in front of the screen.

The memory, data processing means and screen may be contained in a common housing which also contains a power supply for those components and for the image capture means connected thereto by a cable.

In this case, the instrument preferably includes one or more lenses in front of the screen to compensate for close proximity viewing by the user. The lens will then allow the user to focus on the screen when the distance between the latter and the user's eye is less than the user's least distance of distinct vision.

Where the viewing optics include two eyepieces, the screen is preferably one of two such screens, each situated adjacent to the respective eyepiece.

The invention also lies in an ophthalmic instrument comprising image capture means for capturing an image of an eye under examination, data processing means for converting the image into a computer readable file and a connector for detachably connecting the data processing means to a portable memory device to enable said file to be recorded on the device.

Said connector may, for example, comprise a memory card slot or a USB socket.

Preferably, either of the aforesaid instruments comprises an indirect, head mounted ophthalmoscope.

Preferably, the instrument includes a head band for mounting the instrument on the head of a user, and a display screen which is carried by the head band and connected, in use, to the memory, wherein the display screen is operable to display the images stored in the memory to enable the user to view said images after removing the head band.

Thus the user, having operated the instrument and obtained video footage or still images, can then quickly and conveniently view this material when he/she removes the instrument from his or her head.

Preferably, the display screen is situated at a position spaced from the front of the head band.

Consequently, the moment of force exerted by the display on the head band need not is reinforce that exerted by the rest of the instrument.

Preferably, the display screen is situated at the rear of the head band. The display screen, when in this position, will produce a moment of force which counteracts that produced by the part of the instrument at the front of the head band.

The instrument may conveniently be one which, in use, carries its own power source, such as one or more electric batteries. Accordingly, the instrument may include a battery housing (for containing one or more batteries) mounted on the rear of the head band, the display screen being mounted on the housing.

Conveniently, the battery housing comprises a battery pack containing one or more batteries.

Preferably, the display screen comprises a display module which is releasably mountable on the instrument.

The module may conveniently contain said memory.

Consequently, the user, having viewed captured images on the display screen can simply detach the module and connect it to a computer (via, for example, a USB male connector on the module plugged into a USB socket in the computer).

BRIEF DESCRIPTION OF THE DRAWINGS

The invention will now be described, by way of example only, with reference to the accompanying drawings in which.

DETAILED DESCRIPTION

Figure 1:
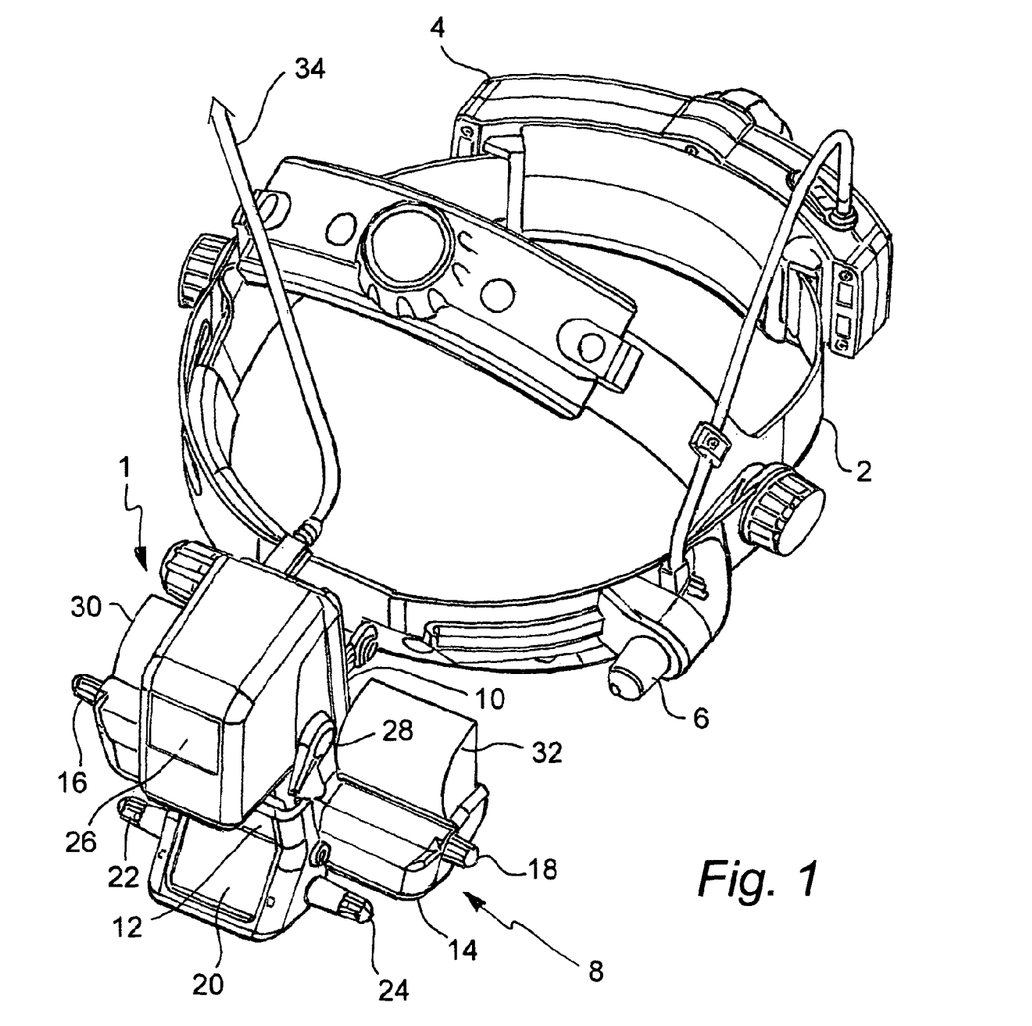
FIG. 1 is an isometric view of a first embodiment of ophthalmoscope (with headband) in accordance with the invention.

With reference to FIG. 1, the first embodiment of instrument in accordance with the invention comprises an indirect ophthalmoscope generally referenced 1 attached to the front of a headband 2 which enables the instrument to be mounted on the head of a user. The rear of the headband 2 carries a battery pack 4 which provides power for operating a light source in the ophthalmoscope 1. The intensity of light emitted by that source can be controlled by an intensity control 6 on the headband 2.

The ophthalmoscope 1 comprises a housing 8 which is in the general shape of an inverted T. The housing contains illumination optics (including the light source mentioned above) and binocular viewing optics.

The illumination optics are contained within the vertical stem 10 of the housing and, in addition to the light source, include an angled mirror positioned under the light source to reflect light from the latter out to a window 12 in the front of the housing 1.

The mirror is positioned immediately above viewing optics contained within the crosspiece 14 of the housing 8. Two side controls 16 and 18 enable the angle of the illumination mirror to be adjusted.

The illumination and viewing optics (and associated controls) of the instrument are as described in the applicant's US patent specification number U.S. Pat. No. 6,280,033.

An angled half-silvered mirror 20 is situated in front of the viewing optics on a mount which enables the angle of the mirror 20 to be adjusted by means of two side controls 22 and 24. The mirror 20 reflects light incident thereon up into a video camera 26 situated in the stem 10 immediately above the mirror 20. The adjustment provided by the controls 24 and/or 22 enables the user of the ophthalmoscope to adjust the field of view of the image detected by the camera so that it coincides as far as possible with what is being seen by the user through the viewing optics.

In use, 30% of the light incident on the mirror 20 is reflected up into the camera, the remaining light passing to the viewing optics, so that the mirror does not unduly degrade the image seen through the viewing optics. The features of the ophthalmoscope 1 thus far described are also present on the current applicant's existing KEELER VANTAGE PLUS LED DIGITAL™ ophthalmoscope. The control knob 28 on the side of the stem 10 is for adjusting the width of the illuminating beam produced by the illumination optics, in a known fashion.

The crosspiece 14 of the housing 8 also accommodates two eyepieces (not visible in FIG. 1), one for each of the user's eyes. Immediately above these eyepieces, on top of the crosspiece 14 there are provided two local LCD display screens 30 and 32, each of which is operable to display the image detected by the camera 26. A respective converging lens (not visible in FIG. 1) is situated in front of each of the screens, to enable the user to focus on the images displayed on the screens while wearing the ophthalmoscope. It will be appreciated that since the screens are immediately above the eyepieces, the user can readily switch from viewing the image of the eye under examination through the viewing optics to viewing the images displayed on the screens 30 and 32, so that the user may more easily adjust the controls 22 and/or 24 to make those images correspond to a reasonable extent.

The illumination optics, viewing optics, and the arrangement of the camera and half-silvered mirror are substantially the same as the corresponding parts of the current applicant's existing KEELER VANTAGE PLUS DIGITAL™ ophthalmoscope.

The camera 26 is a USB2 powered board camera.

Figure 2:
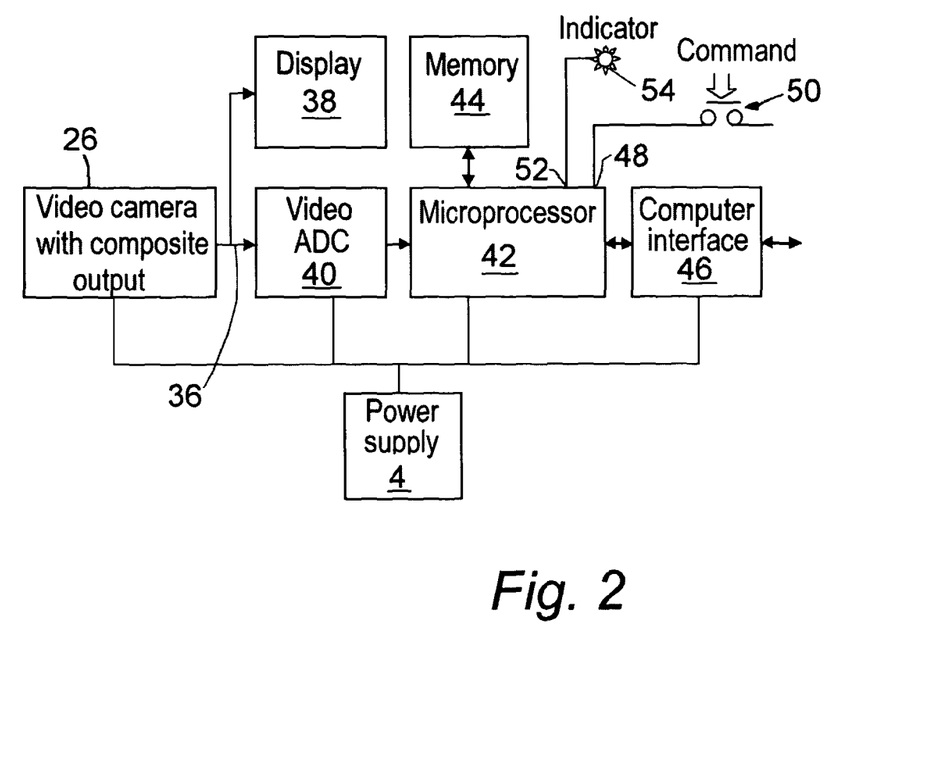
FIG. 2 is a block circuit diagram of various of the components of the ophthalmoscope of FIG. 1.

With reference to FIG. 2 the camera generates an analogue video composite output signal which is split at circuit junction 36 so that the signal can be supplied to the display screens 30 and 32 and associated driving circuitry (collectively denoted by reference 38) and to a analogue to digital video signal converter (ADC) 40. The video ADC 40 converts the video composite signal into a digital data stream which is is supplied to a microprocessor 42. The microprocessor 42 is operable to compress the input data stream and convert it into computer readable files in a known way. The microprocessor 42 is, in turn, connected to a solid state memory 44, and the microprocessor 42 is also connected to a computer interface circuitry 46 which provides a USB socket for connection to a USB lead 34 via which the microprocessor 42 (and thus memory 44) can be connected to and controlled by an external computer.

The microprocessor 42 includes an input 48 for a command signal, connected to a record button 50 situated in a suitable external position on the ophthalmoscope housing, to enable the user to commence or interrupt the recording of footage captured by the camera 26. An output 52 of the microprocessor 42 is connected to an indicator LED 54 which is illuminated when the system is in record mode.

As can be seen from FIG. 2, the power supply for the camera, the display, the ADC, the microprocessor, the memory card and the indicator is obtained from the battery pack 4.

In use, the ophthalmoscope 1 is not connected to an external computer and is operated by the user in a similar fashion to a conventional ophthalmoscope. However, if the user wishes to record footage of an examination, the user will initially check the images being detected by the camera 126, using the screens 30 and 32, and will make any necessary adjustments via the controls 22 or 24 so that the image detected by the camera 26 corresponds to what is being viewed through the viewing optics.

Recording of footage of the examination can then be initiated by pressing the button 50 so that the digital data stream from the video ADC 40 is processed by the microprocessor 42 which writes the compressed image data into the memory 44. When the button 50 is pressed again, recording ceases and the microprocessor 42 converts the data written into the memory 44 into a computer readable file which is then also written into memory 44.

After the ophthalmoscope has been used, it can be connected via the cable 34 to an external computer to which the ophthalmoscope appears as a mass storage device with one or more files (in the memory 44) containing the video footage. Thus the computer can download those files for subsequent viewing and analysis. It will be appreciated that the components illustrated in FIG. 2 are similar in form and function to corresponding components of other conventional digital video and storage systems, such as can be found on, for example, certain dedicated digital video cameras and multi-purpose personal digital electronic devices such as mobile phones and personal music players.

Thus video footage can be captured by the ophthalmoscope 1 when it is not connected to an external computer. In addition, when the footage is subsequently downloaded onto a separate computer it is transferred as one or more pre-stored files rather than as streamed video data. Accordingly, limitations in the rate of transfer of data from the ophthalmoscope to the computer will not affect the resolution or frame rate of the captured video footage since the download can occur over a period which is longer than the duration of the footage.

Figure 3:
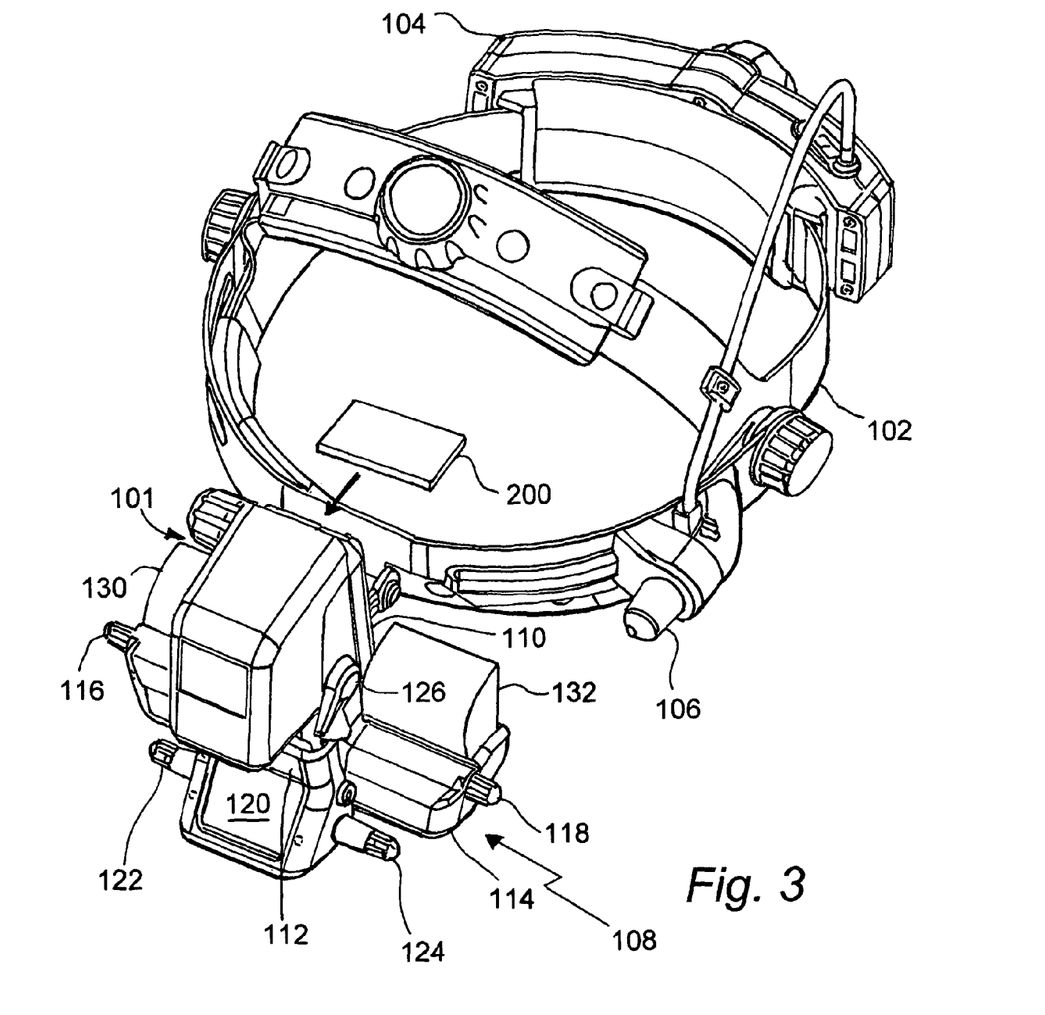
FIG. 3 is a view, corresponding to FIG. 1, of a second embodiment of ophthalmoscope (with headband) in accordance with the invention.

The embodiment of ophthalmoscope shown in FIG. 3 is identical in many respects to the first embodiment of ophthalmoscope and corresponding components have therefore been denoted by the reference numerals of FIG. 1, raised by 100.

However, in this case, the ophthalmoscope 101 does not include an on-board memory but instead has a memory card read/write device for receiving a removable solid state memory card 200. The memory card and associated read/write device function in the same way as the memory 44 shown in FIG. 2. However, when data is to be transferred, the memory card is simply removed from the ophthalmoscope 101 and inserted into a reader in or connected to the external computer. The second embodiment could be modified so that the memory card is replaced by a USB memory stick insertable into a USB socket in the ophthalmoscope 101. Many computers would be compatible with such a memory device without the need for the connection to a dedicated memory card reader. In this embodiment, there is no circuitry corresponding to the block 46 of FIG. 2. The ophthalmoscope does not need to be connected directly to a computer for the captured footage to be transferred.

Figure 4:
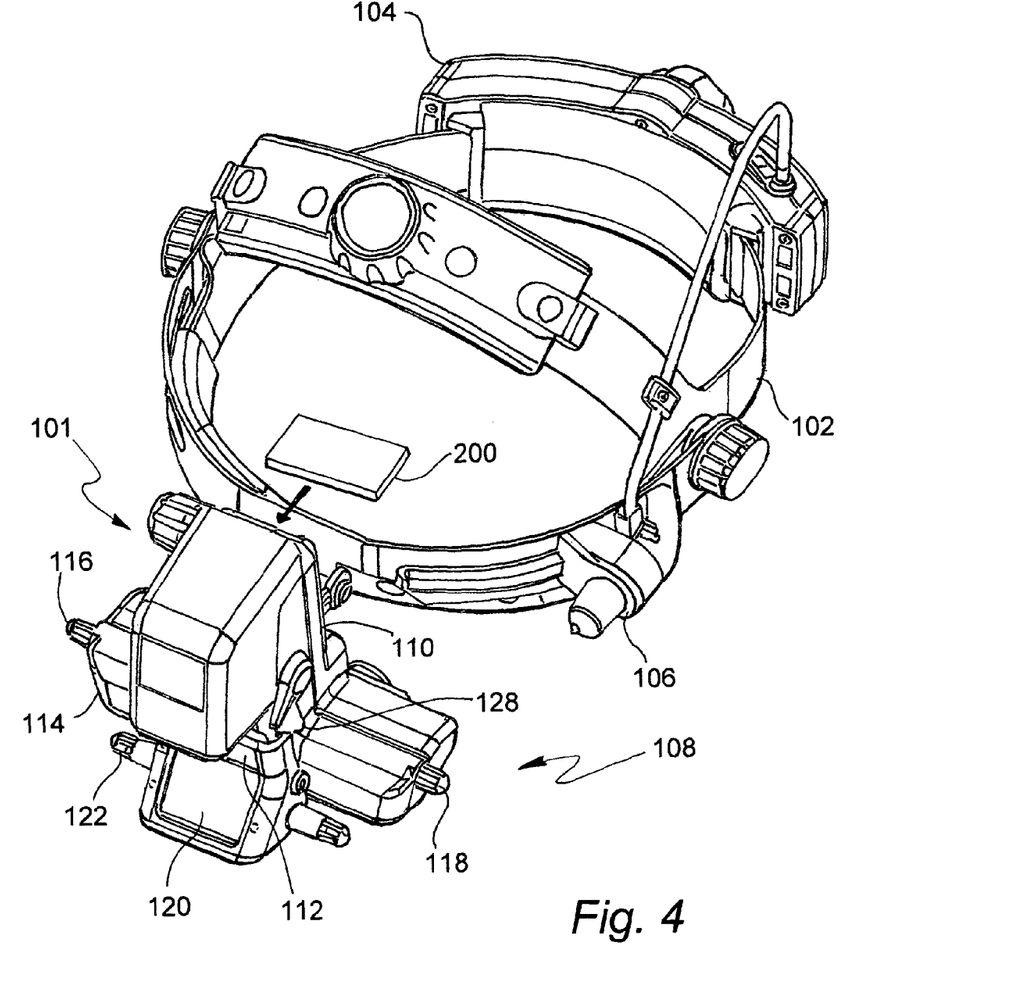
FIG. 4 is a view, corresponding to FIG. 1, of a modified version of the is ophthalmoscope of FIG. 3.

The embodiment shown in FIG. 3 can be modified in the way shown in FIG. 4 in which the viewing screens 30 and 32 have been omitted, to provide a cheaper product.

Figure 5:
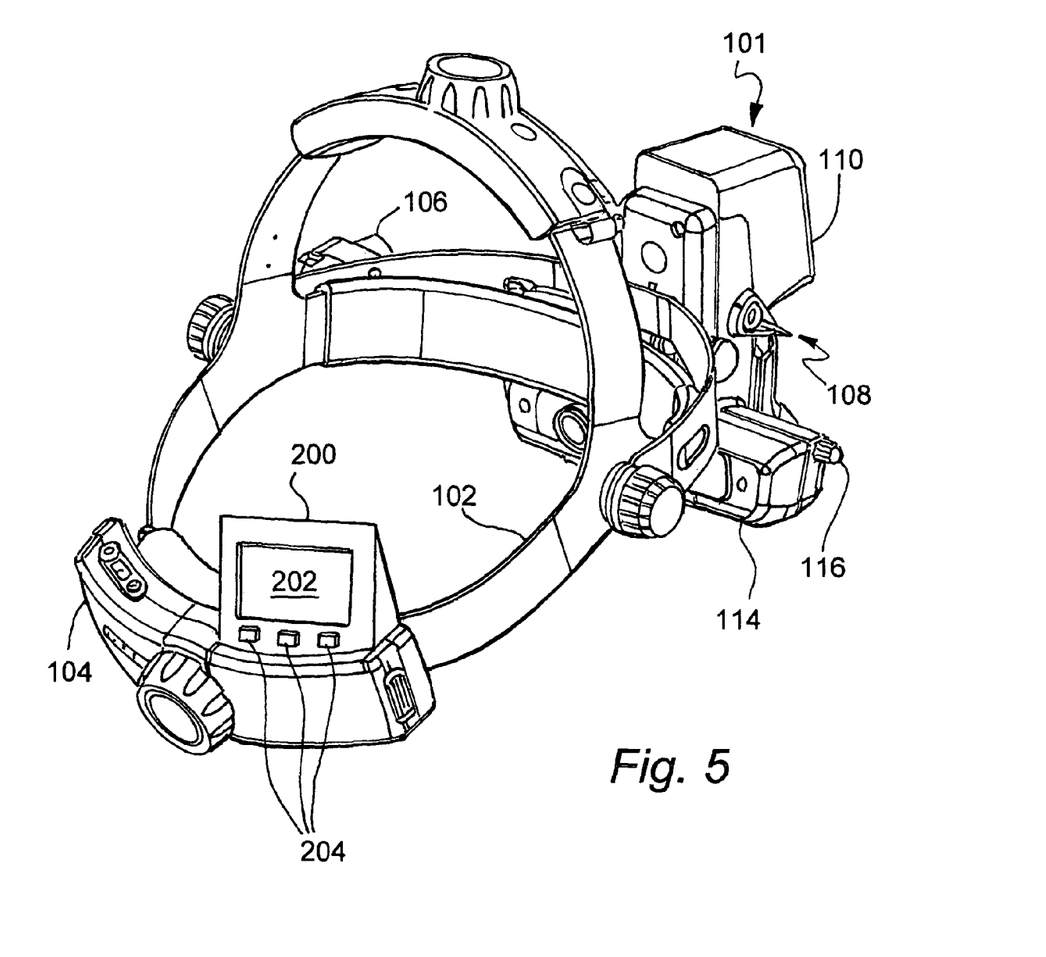
FIG. 5 is an isometric view, from behind, of another modified version of the ophthalmoscope.

The further modified version of ophthalmoscope shown in FIG. 5 has many features common with the ophthalmoscope of FIG. 4, and these are denoted by the same reference numerals as are used in FIG. 4.

The arrangement shown in FIG. 5 differs from that shown in FIG. 4 in that the ophthalmoscope itself does not have a slot for a memory card, and in that a display screen forming part of a display module 200 is mounted on top of the battery pack 104. The battery pack 104 and the underside of the module 200 are provided with interlocking formations (not shown) which enable the module 200 to be releasably attached to the top of the pack 104, and which include power and data contacts for supplying power from the pack 104 to operate the display screen, referenced 202 of the module 200 and to transmit data representative of the images captured by the camera to the screen 200. The data connection links a screen driver (not shown) in the module 200 to the microprocessor 42 via a computer interface such as the interface 46, and the associated formations could therefore, for example, comprise a USB plug on the module 200 which cooperates with a socket in the top of the battery pack 104 or vice versa. The formations that mechanically retain the module 200 on the pack 104 may, for example, comprise male latching members (e.g. pawls) on the underside of the module 200 which engage corresponding apertures in the top of the pack 104 and can be released therefrom by a button (not shown) on the module 200 is linked to the male latching formations in such a way that pushing the button moves those formations until they are clear of the edges of the aperture to allow the module 200 to be removed.

The module 200 may include a memory (not shown) which stores image data transmitted to the module 200 from the camera via the microprocessor. Additionally or alternatively, the ophthalmoscope 101 may include an internal memory such as the memory 44 of the embodiment shown in FIG. 2.

In use, the user operates the camera in the same way as with the other versions of the invention. Once the user has finished using the instrument, he will remove it, and can view the recorded video data on the screen 202 in response to inputs via control buttons 204 on the front of the module 200. Those control buttons may control normal playback options (either by each having a dedicated function such as start/stop or by enabling a cursor to be moved around a menu displayed on the screen 202. On removal of the instrument, the user will be holding the band 102, and so will be able easily to view the screen 202 and operate the buttons 204.

Thus images and videos can be reviewed by the user after completion of an examination using the replay facilities, allowing quick assessment of the quality of the captured data without the need to use a PC. Additionally or alternatively, the captured video footage can be reviewed/viewed by observers watching the screen 202 during an examination.

The screen 202 can be any suitable display screen for displaying video or still images, for example an LCD, LED or OLED screen.

The invention claimed is:

1. An ophthalmic instrument for viewing an eye under examination, wherein the ophthalmic instrument includes an image capture device for capturing an image of said eye and an image display screen which is operable to display images captured by the image capture device for viewing by a user of the instrument, wherein the ophthalmic instrument includes viewing optics through which the user may also view the eye under examination, wherein the viewing optics include an eyepiece and the screen is located on the ophthalmic instrument adjacent the eyepiece, wherein the ophthalmic instrument includes one or more devices in front of the image display screen to compensate for close proximity viewing by the user, wherein the ophthalmic instrument includes a data processor for converting said image captured by the image capture device into a computer readable file, wherein the ophthalmic instrument carries a memory for storing said file for subsequent display and/or transfer to a computer, wherein the ophthalmic instrument includes a head band for mounting the ophthalmic instrument on the head of a user, and a further image display screen which is carried by the head band and connected, in use, to the memory, and wherein the further image display screen is operable to display the images stored in the memory to enable the user to view said images after removing the head band, the further image display screen being situated at the rear of the head band for viewing from the rear of the head band.

2. The ophthalmic instrument according to claim 1 in which the image capture device comprises a video camera.

3. The ophthalmic instrument according to claim 1 in which the memory comprises a portable memory device which is detachable from the ophthalmic instrument and is connectable to a computer to be read thereby.

4. The ophthalmic instrument according to claim 3 in which the portable memory device is a solid state device.

5. The ophthalmic instrument according to claim 4 in which the memory device comprises a memory card or USB stick.

6. The ophthalmic instrument according to claim 3, wherein the ophthalmic instrument includes a connector for detachably connecting the data processor to the portable memory device to enable said file to be recorded on the device.

7. The ophthalmic instrument according to claim 6 in which the connector comprises a memory card slot or a USB socket.

8. The ophthalmic instrument according to claim 6 in which the ophthalmic instrument comprises an indirect, head mounted ophthalmoscope.

9. The ophthalmic instrument according to claim 1 in which the memory is built into the ophthalmic instrument.

10. The ophthalmic instrument according to claim 1 in which the viewing optics include two eyepieces, and the image display screen is one of two such screens, each situated adjacent to a respective one of the two eyepieces.

11. The ophthalmic instrument according to claim 1, in which the ophthalmic instrument is provided with a further image display screen on which the user may view the image being captured by the image capture device, wherein the further image display screen is separate from a body of the ophthalmic instrument and includes means for mounting and retaining the screen in the vicinity of one of the user's hands.

12. The ophthalmic instrument according to claim 11 in which the further image display screen is attached to a hand held lens or provided with a strap or band for attachment of the further image display screen to the user's forearm.

13. The ophthalmic instrument according to claim 1 in which the memory, data processor and further image display screen are contained in a common housing which also contains a power supply for those components and for the image capture device, which image capture device is connected to the power supply.

14. The ophthalmic instrument according to claim 1 in which the ophthalmic instrument includes a battery housing mounted on the rear of the head band, the further image display screen being mounted on the battery housing.

15. The ophthalmic instrument according to claim 14 in which the battery housing comprises a battery pack containing one or more batteries.

16. The ophthalmic instrument according to claim 1 in which the further image display screen comprises a display module releasably mountable on the instrument.

17. The ophthalmic instrument according to claim 16 in which the module contains said memory.

18. The ophthalmic instrument according to claim 1 in which the ophthalmic instrument comprises an indirect ophthalmoscope.

19. An ophthalmic instrument for viewing an eye under examination, wherein the ophthalmic instrument includes an image capture device for capturing an image of said eye and a data processor for converting said image into a computer readable file, the ophthalmic instrument carries a memory for storing said file for subsequent display and/or transfer to a computer, the ophthalmic instrument includes a head band for mounting the ophthalmic instrument on the head of a user, and an image display screen which is carried by the head band and connected, in use, to the memory, the image display screen is operable to display the images stored in the memory to enable the user to view said images after removing the head band, the image display screen is situated at the rear of the head band for viewing from the rear of the head band, wherein the ophthalmic instrument is provided with a further image display screen on which the user may view the images being captured by the image capture device, the ophthalmic instrument includes viewing optics through which the user may view the eye under examination, the viewing optics include an eyepiece, the further image display screen being located on the ophthalmic instrument adjacent said eyepiece, and wherein the ophthalmic instrument includes one or more lenses in front of the further image display screen to compensate for close proximity viewing by the user.

20. An ophthalmic instrument for viewing an eye under examination, wherein the ophthalmic instrument includes an image capture device for capturing an image of said eye and a data processor for converting said image into a computer readable file, the ophthalmic instrument carries a memory for storing said file for subsequent display and/or transfer to a computer, the ophthalmic instrument includes a head band for mounting the ophthalmic instrument on the head of a user, and an image display screen which is carried by the head band and connected, in use, to the memory, the image display screen is operable to display the images stored in the memory to enable the user to view said images after removing the head band, the image display screen is situated at the rear of the head band for viewing from the rear of the head band, the ophthalmic instrument is provided with a further image display screen on which the user may view the images being captured by the image capture device, the ophthalmic instrument includes viewing optics through which the user may view the eye under examination, the viewing optics include an eyepiece, the further image display screen being located on the ophthalmic instrument adjacent said eyepiece, and wherein the viewing optics include two eyepieces, and the further image display screen is one of two such screens, each situated adjacent to a respective one of the two eyepieces.

\* \* \* \* \*